(12) United States Patent
Goldstein et al.

(10) Patent No.: US 6,696,471 B2
(45) Date of Patent: Feb. 24, 2004

(54) AMINOPYRROLE COMPOUNDS

(75) Inventors: David Michael Goldstein, San Jose, CA (US); David Mark Rotstein, Sunnyvale, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 1 day.

(21) Appl. No.: 10/231,792

(22) Filed: Aug. 29, 2002

(65) Prior Publication Data

US 2003/0130319 A1 Jul. 10, 2003

Related U.S. Application Data

(60) Provisional application No. 60/316,169, filed on Aug. 30, 2001.

(51) Int. Cl.$^7$ .................. A61K 31/44; C07D 401/04
(52) U.S. Cl. ........................... 514/343; 546/279.1
(58) Field of Search .................. 514/343; 546/279.1

(56) References Cited

FOREIGN PATENT DOCUMENTS

| WO | WO 98/02430 A1 | 1/1998 |
|---|---|---|
| WO | WO 99/57101 A1 | 11/1999 |

*Primary Examiner*—D. Margaret Seaman
(74) *Attorney, Agent, or Firm*—Grant D. Green; Rohan Peries

(57) ABSTRACT

The present invention provides an aminopyrrole compound of the formula:

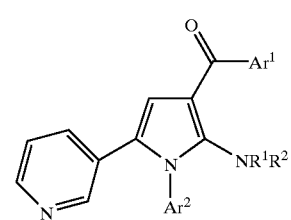

a prodrug, individual isomer, a mixture of isomers or a pharmaceutically acceptable salt thereof, where $R^1$, $R^2$, $Ar^1$ and $Ar^2$ are those defined herein. The present invention also provides methods of using and preparing the aminopyrrole compounds of Formula I.

18 Claims, No Drawings

AMINOPYRROLE COMPOUNDS

CROSS REFERENCE TO RELATED INVENTION

This application claims benefit under Title 35 U.S.C. 119(e) of U.S. Provisional Application No. 60/316,169, filed Aug. 30, 2001, the disclosure of which is herein incorporated by reference.

FIELD OF THE INVENTION

The present invention relates to aminopyrrole compounds and methods for preparing and using the same.

BACKGROUND OF THE INVENTION

TNF and IL-1 have been shown to be central players in the pathological processes underlying many chronic inflammatory and autoimmune diseases. IL-1 is implicated in mediating or exacerbating diseases such as rheumatoid arthritis ((see., Arend, W. P. *Arthritis & Rheumatism* 38(2): 151–160, (1995)), osteoarthritis, bone resorption, toxic shock syndrome, tuberculosis, atherosclerosis, diabetes, Hodgkin's disease (see., Benharroch, D.; et. al. *Euro. Cytokine Network* 7(1): 51–57) and Alzheimer's disease. Excessive or unregulated TNF production has been implicated in mediating or exacerbating diseases such as rheumatoid arthritis ((see., Maini, R. N.; et. al. *APMIS*. 105(4): 257–263, (1997); Feldmann, M., *J. of the Royal College of Physicians of London* 30(6): 560–570, (1996); Lorenz, H. M.; et. al. *J. of Immunology* 156(4): 1646–1653, (1996)) osteoarthritis, spondylitis, sepsis, septic shock ((see., Abraham, E.; et. al. *JAMA*. 277(19):1531–1538, (1997), adult respiratory distress syndrome, asthma ((see., Shah, A.; et. al. *Clin. & Exp. Allergy* 1038–1044, (1995) and Lassalle, P., et. al. *Clin. & Exp. Immunol.* 94(1): 105–110, (1993)), bone resorption diseases, fever ((see., Cooper, A. L., et. al. *Am. J. of Physiology* 267(6 Pt. 2): 1431–1436)), encephalomyelitis, demyelination ((see., Klindert, W. E.; et al. *J. of Neuroimmunol.* 72(2): 163–168, (1997)) and periodontal diseases.

Clinical trials with IL-1 and TNF receptor antagonists have shown that blocking the ability of these cytokines to signal through their receptors leads to significant improvement, in humans, in inflammatory diseases. Therefore, modulation of these inflammation and have positive therapeutic outcomes. It has also been shown that p38 MAP kinase plays an important role in the translational control of TNF and IL-1 and is also involved in the biochemical signaling of these molecules ((see., Lee, J. C., et al. *Nature*. 372 (6508): 739–46, (1994)). Compounds that bind to p38 MAP are effective in inhibiting bone resorption, inflammation, and other immune and inflammation-based pathologies. The characterization of the p38 MAP kinase and its central role in the biosynthesis of TNF and IL-1 have made this kinase an attractive target for the treatment of diseases mediated by these cytokines.

It would therefore be desirable to provide p38 MAP kinase inhibitors and thereby provide a means of combating diseases mediated by pro-inflammatory cytokines such as TNF and IL-1. This invention fulfills this and related needs.

SUMMARY OF THE INVENTION

One aspect of the present invention provides an aminopyrrole compound of the formula:

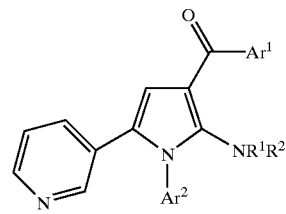

a prodrug, individual isomer, a mixture of isomers or a pharmaceutically acceptable salt thereof and methods for preparing or using the same, wherein each of $Ar^1$ and $Ar^2$ is independently optionally substituted aryl; and each of $R^1$ and $R^2$ is independently hydrogen, alkyl or a nitrogen protecting group.

Another aspect of the present invention provides a method for producing an aminopyrrole compound of the formula:

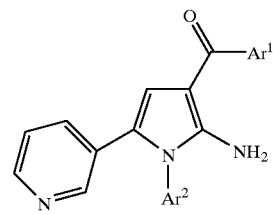

said method comprising forming an aminopyrrole ring system by contacting a cyano compound of the formula:

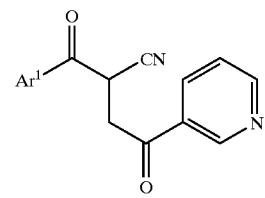

with an arylamine compound of the formula $Ar^2$—$NH_2$ under conditions sufficient to produce the aminopyrrole compound of Formula I,
wherein
each of $Ar^1$ and $Ar^2$ is independently optionally substituted aryl.

Another aspect of the present invention provides a composition comprising a therapeutically effective amount of a compound of Formula I and an excipient.

Still another aspect of the present invention provides a method for inhibiting p38 MAP kinase in a cell comprising administering a compound of Formula I to the cell comprising p38 MAP kinase.

Yet another aspect of the present invention provides a method for treating a disease in a mammal treatable by administration of a p38 MAP kinase inhibitor, comprising administration to the mammal a therapeutically effective amount of a compound of Formula I.

DEFINITIONS

Unless otherwise stated, the following terms used in the specification and claims have the meanings given below:

"Alkyl" means a linear saturated monovalent hydrocarbon moiety of one to six carbon atoms or a branched saturated monovalent hydrocarbon radical of three to six carbon atoms, e.g., methyl, ethyl, propyl, 2-propyl, pentyl, and the like.

"Alkoxy" means a moiety —OR where R is alkyl as defined above, e.g., methoxy, ethoxy, propoxy, 2-propoxy, the like.

"Acyl" means a moiety —C(O)R where R is hydrogen, alkyl, haloalkyl, or heteroalkyl, e.g., acetyl, trifluoroacetyl, and the like.

"Aryl" means a monovalent monocyclic or bicyclic aromatic hydrocarbon radical of 6 to 10 ring atoms e.g., phenyl, 1-naphthyl, 2-naphthyl, and the like.

"Halide" means fluoride, chloride, bromide, or iodide.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Heteroalkyl" means an alkyl moiety as defined above, having one or more, preferably one, two or three, substituents selected from —NR$^a$R$^b$, —OR$^c$ wherein R$^a$, R$^b$ and R$^c$ are independently of each other hydrogen, alkyl, or the corresponding protecting group. Representative examples include, but are not limited to, hydroxymethyl, 3-hydroxypropyl, 1,2-dihydroxyethyl, 2-methoxyethyl, 2-aminoethyl, 2-dimethylaminoethyl, and the like.

"Heteroalkoxy" means a moiety —OR where R is heteroalkyl group as defined above, e.g., 2-hydroxyethoxy, 3-hydroxypropoxy, 2,3-dihydroxypropoxy, 2,3-dihydroxy-1-methylpropoxy, 2-aminoethoxy, and the like.

"Optionally substituted aryl" means an aryl ring as defined above, which is optionally substituted independently with one or more, preferably one or two, substituents selected from alkyl, alkoxy, heteroalkyl, heteroalkyl, halide, cyano, acyl, —NRR' (where R and R' are independently selected from hydrogen, alkyl or acyl), —NHCOR (where R is alkyl),—NRS(O)$_n$R' (where R is hydrogen or alkyl, n is an integer from 0 to 2 and R' is hydrogen, alkyl or heteroalkyl), —NRS(O)$_n$NR'R" (where R is hydrogen or alkyl, n is an integer from 0 to 2 and R' and R" are independently hydrogen, alkyl or heteroalkyl), —S(O)$_n$R (where n is an integer from 0 to 2 and R is hydrogen, alkyl or heteroalkyl), —S(O)$_n$NRR' (where n is an integer from 0 to 2 and R and R' are independently hydrogen, alkyl or heteroalkyl), —COOR, -(alkylene)COOR (where R is hydrogen or alkyl), —CONR'R" or -(alkylene)CONR'R" (where R' and R" are independently hydrogen or alkyl).

"Optionally substituted phenyl" means a phenyl which is optionally substituted independently with one or more, preferably one or two, substituents selected from alkyl, alkoxy, heteroalkyl, heteroalkyl, halide, cyano, acyl, —NRR' (where R and R are independently selected from hydrogen, alkyl or acyl), —NHCOR (where R is alkyl), —NRS(O)$_n$R' (where R is hydrogen or alkyl, n is an integer from 0 to 2 and R' is hydrogen, alkyl or heteroalkyl), —NRS(O)$_n$NR'R" (where R is hydrogen or alkyl, n is an integer from 0 to 2 and R' and R" are independently hydrogen, alkyl or heteroalkyl), —S(O)$_n$R (where n is an integer from 0 to 2 and R is hydrogen, alkyl or heteroalkyl), —S(O)$_n$NRR' (where n is an integer from 0 to 2 and R and R' are independently hydrogen, alkyl or heteroalkyl), —COOR, -(alkylene)COOR (where R is hydrogen or alkyl), —CONR'R" or -(alkylene)CONR'R" (where R' and R" are independently hydrogen or alkyl).

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the heterocyclo group is not substituted with the alkyl group.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DETAILED DESCRIPTION

One aspect of the present invention provides

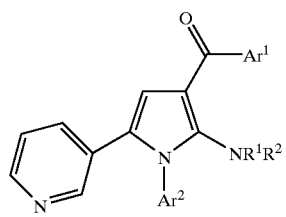

I a prodrug, individual isomer, a mixture of isomers or a pharmaceutically acceptable salt thereof and methods for preparing or using the same, where $Ar^1$, $Ar^2$, $R^1$ and $R^2$ are those defined above.

Preferably, $R^1$ and $R^2$ are hydrogen.

Preferably, $Ar^2$ is an optionally substituted phenyl, more preferably a halide substituted phenyl, and most preferably 4-halophenyl, particularly 4-fluorophenyl.

Preferably, $Ar^1$ is selected from the group consisting of phenyl, alkoxy substituted phenyl, hydroxy substituted phenyl and heteroalkoxy substituted phenyl. More preferably, $Ar^1$ is selected from the group consisting of phenyl, 3-methoxyphenyl, 3-hydroxyphenyl, and 3-(2,3-dihydroxypropoxy)phenyl.

In one embodiment of the present invention, $R^1$ and $R^2$ are hydrogen and $Ar^2$ is optionally subsituted phenyl.

In another embodiment, $R^1$ and $R^2$ are hydrogen and $Ar^2$ is a halide substituted phenyl, preferably 4-fluorophenyl.

Yet in another embodiment, $R^1$ and $R^2$ are hydrogen, $Ar^2$ is 4-fluorophenyl, and $Ar^1$ is selected from the group consisting of phenyl, alkoxy substituted phenyl, hydroxy substituted phenyl and heteroalkoxy substituted phenyl. Preferably $Ar^1$ is heteroalkoxy substituted phenyl. More preferably, $Ar^1$ is 3-(2,3-dihydroxypropoxy)phenyl.

Still yet in another embodiment, $R^1$ and $R^2$ are hydrogen, $Ar^2$ is 4-fluorophenyl, and $Ar^1$ is phenyl, 3-methoxyphenyl, 3-hydroxyphenyl or 3-(2,3-dihydroxypropoxy)phenyl.

In another embodiment of the invention, $R^1$ and $R^2$ are hydrogen and $Ar^1$ is optionally substituted phenyl. Preferably, $Ar^1$ is phenyl, alkoxy substituted phenyl, hydroxy substituted phenyl or heteroalkoxy substituted phenyl. Preferably $Ar^1$ is heteroalkoxy substituted phenyl. More preferably, $Ar^1$ is 3-(2,3-dihydroxypropoxy)phenyl. Within this embodiment, $Ar^2$ is preferably halide substituted phenyl, preferably 4-fluorophenyl.

Combinations of the preferred groups described above also form other preferred embodiments. Thus, for example, preferred substituents $R^1$ and $R^2$ are also preferred substituents of compounds having preferred substituents $Ar^1$ and/or $Ar^2$.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. Furthermore, as stated above, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, or example, Berge et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge et al., "Pharmaceutical Salts," *J. of Pharmaceutical Science*, 1977, 66, 1–19).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

Exemplary compounds of the present invention are shown in Table 1 below:

TABLE 1

Exemplary compounds of Formula I

| Cpd # | $R^1$ | $R^2$ | $Ar^1$ | $Ar^2$ |
|---|---|---|---|---|
| 1 | H | H | phenyl | 4-fluorophenyl |

TABLE 1-continued

Exemplary compounds of Formula I

| Cpd # | R¹ | R² | Ar¹ | Ar² |
|---|---|---|---|---|
| 2 | H | H | 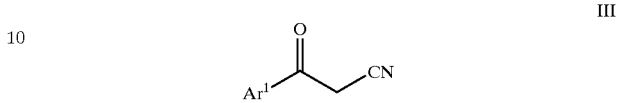 | 4-fluorophenyl |
| 3 | H | H | 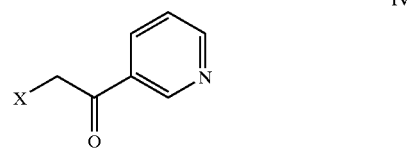 | 4-fluorophenyl |
| 4 | H | H | 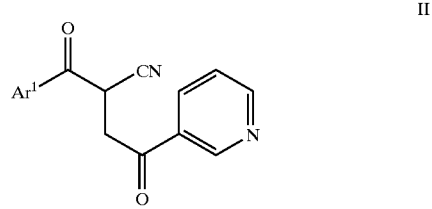 | 4-fluorophenyl |

Preparation of Compounds of Formula I

Compounds of the present invention can be made by the methods described below. The starting materials and reagents used in preparing these compounds are either available from commercial suppliers such as Aldrich Chemical Co., (Milwaukee, Wis., U.S.A), Bachem (Torrance, Calif., U.S.A), Emka-Chemie, or Sigma (St. Louis, Mo., U.S.A) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be readily apparent to one skilled in the art having referred to this disclosure.

The starting materials and the intermediates of the reaction can be isolated and purified if desired using conventional techniques, including but not limited to filtration, distillation, crystallization, chromatography, and the like. Such materials can be characterized using conventional means, including physical constants and spectral data.

In one embodiment, Ar² is 4-fluorophenyl.

In another embodiment, Ar² is 4-fluorophenyl and Ar¹ is alkoxy substituted phenyl.

In yet another embodiment, Ar² is 4-fluorophenyl and Ar¹ is alkoxy substituted phenyl, and the method further comprises converting the alkoxy substituent to a hydroxy substituent by contacting the aminopyrrole compound of Formula I with a Lewis acid under conditions sufficient to produce the aminopyrrole compound of Formula I wherein Ar¹ is a hydroxy substituted phenyl.

Still in another embodiment, the method further comprises alkylating the hydroxy group of Ar¹ by contacting the aminopyrrole compound of Formula I, wherein Ar¹ is a hydroxy substituted phenyl, with a heteroalkyl compound comprising a leaving group under conditions sufficient to produce the aminopyrrole compound of Formula I, wherein Ar¹ is a heteroalkoxy substituted phenyl.

Yet still in another embodiment, the cyano compound of Formula II is produced by contacting an aroyl acetonitrile derivative of the formula:

$$\underset{Ar^1}{\overset{O}{\underset{\|}{C}}}\hspace{-2pt}\diagdown\hspace{-2pt}CN \qquad III$$

with a 3-haloacetylpyridine of the formula:

$$\text{IV}$$

in the presence of a base under conditions sufficient to produce said cyano compound of Formula II, wherein Ar¹ is optionally substituted aryl; and X is a leaving group.

One particular method for producing compounds of Formula I comprises forming an aminopyrrole ring system by contacting a cyano compound of the formula:

$$\text{II}$$

with an arylamine compound of the formula Ar²—NH₂ under conditions sufficient to produce the aminopyrrole compound of Formula I, where Ar¹ and Ar² are those defined above. The aminopyrrole ring forming reaction is typically an acid catalyzed cyclization reaction. Preferably, the acid is a strong acid having pH of about 2 or less. Suitable acid catalysts include inorganic acids, such as sulfuric acid, phosphoric acid, HCl, HBr, HI, as well as Lewis acids such are AlCl₃, BBr₃, BCl₃ and the like. It should be appreciated that when a proton source is available Lewis acids can also generate inorganic protic acid which can also catalyze the cyclization reaction.

The cyclization is generally carried out in a polar solvent such as ethanol, isopropanol and the like. The cyclization reaction temperature depends on a variety of factors including the particular acid catalyst utilized, reaction solvent, reactivity of the starting material, etc. Typically, the cyclization reaction temperature is at least about 80° C. In practice, the cyclization reaction is carried out under the refluxing conditions of the reaction solvent.

The cyclization reaction time also depends on a variety of factors such as those described above including the reaction temperature. Generally, however, the cyclization reaction time is at least about 8 hrs under refluxing condition. Typically, the cyclization reaction time is from about 6 hrs to about 16 hours.

The cyano compound of Formula II can be readily prepared by contacting an aroyl acetonitrile derivative of the formula:

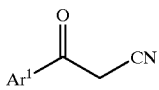

III with a 3-haloacetylpyridine of the formula:

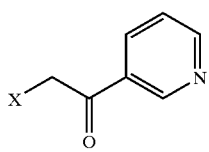

IV in the presence of a base under conditions sufficient to produce the cyano compound of Formula II, where $Ar^1$ is that defined above and X is a leaving group such as halide, preferably bromide or chloride. Suitable bases for the substitution reaction typically are none nucleophilic bases. Preferably, the base is sufficiently strong enough to deprotonate the aroyl acetonitrile derivative of Formula III. Suitable bases include metal hydrides, metal tert-butoxides and the like. Because a strong base is typically used, the initial deprotonation reaction between the base and the aroyl acetonitrile derivative of Formula III is an exothermic reaction. As such, the reaction temperature is generally kept at about 0° C. or less. Typical reaction solvent is an aprotic solvent, such as tetrahydrofuran, and diethyl ether.

Methods of preparing compounds of Formula I can further include modifying the aryl group $Ar^1$ or $Ar^2$. For example, when the aryl group $Ar^1$ contains a substituent, methods of the present invention can include replacing or modifying the substituent on the aryl group. This is particularly applicable where $Ar^1$ is substituted with one or more of amino, carbonyl, hydroxy and alkoxy groups. When $Ar^1$ is substituted with an alkoxy group, the alkoxy group can be converted to a hydroxy group by contacting the compound of Formula I with a Lewis acid. Suitable Lewis acids include those described in *Protective Groups in Organic Synthesis*, 3rd edition, T. W. Greene and P. G. M. Wuts, John Wiley & Sons, New York, 1999, which is incorporated herein by reference in its entirety.

The free hydroxy group can then be substituted (e.g., alkylated) with a desired substituent. For example, by contacting the hydroxy group with a heteroalkyl compound comprising a leaving group provides an aminopyrrole compound of Formula I, where $Ar^1$ is a heteroalkoxy substituted phenyl.

Utility, Testing, and Administration
Utility

Compounds of the present invention have a wide variety of pharmaceutical activities. For example, present inventors have found that compounds of the present invention are p38 MAP kinase inhibitors. Thus the compounds are useful for the treatment of inflammatory diseases, particularly arthritis.

Therefore, compounds of the present invention are useful in the treatment of a disease which is mediated by p38 MAP kinase, including rheumatoid arthritis, osteoarthritis, spondylitis, bone resorption diseases, sepsis, septic shock, toxic shock syndrome, endotoxic shock, tuberculosis, atherosclerosis, diabetes, adult respiratory distress syndrome, chronic pulmonary inflammatory disease, fever, periodontal diseases, ulcerative colitis, pyresis, Alzheimer's and Parkinson's diseases.

Testing

The ability of the compounds of the present invention to inhibit p38 MAP kinase was demonstrated by the in vitro assay described in Example 4. The ability of the compounds of the present invention to inhibit the release of TNF-α was demonstrated by the in vitro and the in vivo assays described in detail in Examples 5 and 6, respectively. The anti-inflammatory activity of the compounds of this invention can be determined utilizing adjuvant induced arthritis in rats assay described in Example 7.

Administration and Pharmaceutical Compositions

In general, the compounds of this invention are administered in a therapeutically effective amount by any of the accepted modes of administration for agents that serve similar utilities. The actual amount of the compound of this invention, i.e., the active ingredient, typically depends on numerous factors such as the severity of the disease to be treated, the age and relative health of the subject, the potency of the compound used, the route and form of administration, and other factors.

Therapeutically effective amounts of compounds of the present invention can range from approximately 0.1–50 mg per kilogram body weight of the recipient per day; preferably about 1–30 mg/kg/day. Thus, for administration to a 70 kg person, the dosage range would most preferably be about 70 mg to 2.1 g per day.

In general, compounds of the present invention are administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 3.

EXAMPLES

The following examples are offered to illustrate, but not to limit the claimed invention.

Example 1

This example illustrates a method for producing [2-amino-1-(4-fluorophenyl)-5-pyridin-3-yl-1h-pyrrol-3-yl]-phenylmethanone.

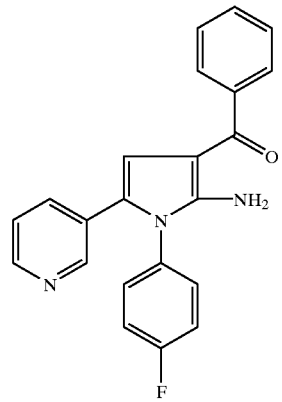

Step a: preparation of 2-benzoyl-4-oxo-4-pyridin-3-yl-butyronitrile

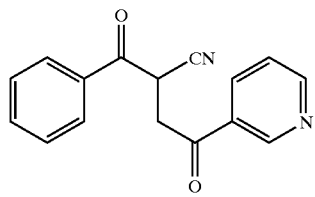

To 3.0 g (21 mmol) of benzoyl acetonitrile in 50 mL of THF, cooled in a wet ice bath, was added 0.84 g (21 mmol) of sodium hydride (60% oil dispersion). After 1 h, added 2.8 g (10 mmol) of 3-bromoacetylpyridine hydrobromide. After 3 h, poured the reaction mixture into brine, extracted with ethyl acetate, dried over sodium sulfate, concentrated under reduced pressure and purified by flash chromatography (gradient elution: 40–80% ethyl acetate/hexane) to give 2.6 g (93%) of 2-benzoyl-4-oxo-4-pyridin-3-yl-butyronitrile (MH$^+$=265).

Step b: preparation of preparation of [2-amino-1-(4-fluorophenyl)-5-pyridin-3-yl-1h-pyrrol-3-yl]-phenylmethanone

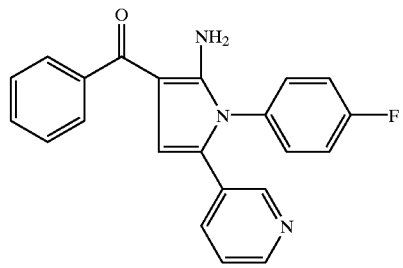

To a solution of 2.6 g (9.8 mmol) of 2-benzoyl-4-oxo-4-pyridin-3-yl-butyronitrile and 0.93 mL (9.8 mmol) of 4-fluoroaniline in 30 mL of ethyl alcohol was added 6 drops of concentrated HCl and the mixture was heated to reflux. After 16 h, the reaction was cooled to room temperature and a yellow solid was isolated by filtration. The solid was recrystallized from methyl alcohol/ethyl acetate to afford 1.5 g (42%) of [2-amino-1-(4-fluorophenyl)-5-pyridin-3-yl-1h-pyrrol-3-yl]-phenylmethanone (mp=231.4–231.8). Treatment of an ethyl acetate solution of this free base with HCl/ether afforded [2-amino-1-(4-fluorophenyl)-5-pyridin-3-yl-1h-pyrrol-3-yl]-phenylmethanone hydrochloride salt (mp 218–222).

Example 2

This example illustrates a method for producing [2-amino-1-(4-fluorophenyl)-5-pyridin-3-yl-1h-pyrrol-3-yl]-3-{[2(s), 3-dihydroxypropoxy]phenyl}-methanone.

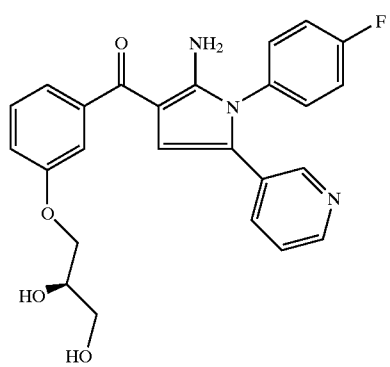

Step a: preparation of 2-(3-methoxybenzoyl)-4-oxo-4-pyridin-3-yl-butyronitrile

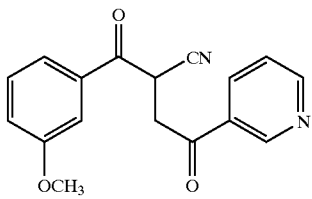

To 1.3 g (7.5 mmol) of 3-methoxybenzoyl acetonitrile in 30 mL of THF, cooled in a wet ice bath, was added 0.3 g (7.5 mmol) of sodium hydride (60% oil dispersion). After 1 h, added 1.0 g (3.6 mmol) of 3-bromoacetylpyridine hydrobromide. After 3 h, poured the reaction mixture into brine, extracted with ethyl acetate, dried over sodium sulfate, concentrated under reduced pressure and purified by flash chromatography (gradient elution: 40–100% ethyl acetate/hexane) to give 0.95 g (43%) of 2-(3-methoxybenzoyl)-4-oxo-4-pyridin-3-yl-butyronitrile (MH$^+$=295).

Step b: preparation of [2-amino-1-(4-fluorophenyl)-5-pyridin-3-yl-1h-pyrrol-3-yl]-3-(methoxyphenyl)methanone

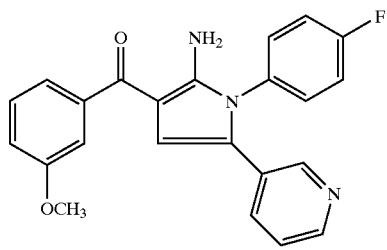

A mixture of 3.0 g (10.2 mmol) of 2-(3-methoxybenzoyl)-4-oxo-4-pyridin-3-yl-butyronitrile, 0.97 mL (10.2 mmol) of 4-fluoroaniline and 6 drops of concentrated HCl in 30 mL of ethyl alcohol were heated at reflux. After 16 h, the reaction mixture was cooled to room temperature, concentrated under reduced pressure, diluted with aqueous sodium bicarbonate and extracted with ethyl acetate. The extracts were washed with brine, dried over sodium sulfate, concentrated under reduced pressure and purified by flash chromatography (gradient elution: 20–40% ethyl acetate/hexane) to give 1.0 g (25%) of [2-amino-1-(4-fluorophenyl)-5-pyridin-3-yl-1h-pyrrol-3-yl]-3-(methoxyphenyl)methanone (MH$^+$=388).

Step c: preparation of [2-amino-1-(4-fluorophenyl)-5-pyridin-3-yl-1h-pyrrol-3-yl]-3-(hydroxyphenyl)methanone

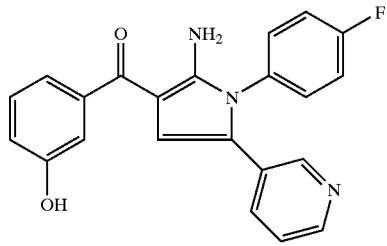

To a solution of 1.0 g (2.6 mmol) of [2-amino-1-(4-fluorophenyl)-5-pyridin-3-yl-1h-pyrrol-3-yl]-3-methoxyphenyl)methanone in 25 mL of dichloromethane, cooled in a wet ice bath, was added 15.5 mL (155 mmol) of boron tribromide (1.0 M in dichloromethane). The reaction was allowed to warm to room temperature. After 16 h, the reaction was recooled in a wet ice bath and water was added dropwise. The pH of the reaction mixture was adjusted to 10 with concentrated ammonium hydroxide and then extracted with dichlormethane. The organic extracts were washed with brine, dried over sodium sulfate, concentrated under reduced pressure and purified by flash chromatography (gradient elution: 40–80% ethyl acetate/hexane) to afford 0.6 g (62%) of [2-amino-1-(4-fluorophenyl)-5-pyridin-3-yl-1h-pyrrol-3-yl]-3-(hydroxyphenyl)methanone (mp=240.3–242.5).

Step d: preparation of [2-amino-1-(4-fluorophenyl)-5-pyridin-3-yl-1h-pyrrol-3-yl]-[3-(2,2-dimethyl-[1,3]dioxolan-4-(s)-ylmethoxy)-phenyl]-methanone

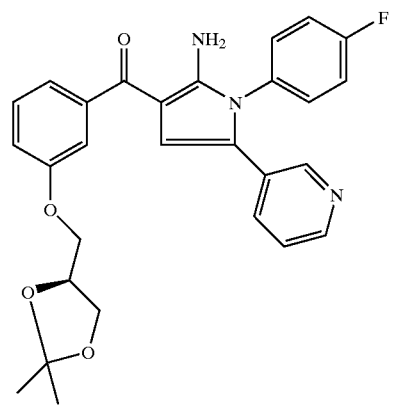

A mixture of 0.6 g (1.6 mmol) of [2-amino-1-(4-fluorophenyl)-5-pyridin-3-yl-1H-pyrrol-3-yl](hydroxyphenyl)methanone, 1.06 g (3.7 mmol) of L-α,β-isopropylideneglycerol-γ-tosylate and 1.2 g (8.7 mmol) of potassium carbonate in 10 mL of DMF was heated at 80°. After 16 h, the reaction mixture was cooled to room temperature, poured into brine and extracted with ethyl acetate. The extracts were dried over sodium sulfate, concentrated under reduced pressure and purified by flash chromatography (gradient elution: 15–50% ethyl acetate/hexane) to give 0.7 g (90%) of [2-amino-1-(4-fluorophenyl)-5-pyridin-3-yl-1H-pyrrol-3-yl]-[3-(2,2-dimethyl-[1,3]dioxolan-4(S)-ylmethoxy)-phenyl]-methanone.

Step e: preparation of [2-amino-1-(4-fluorophenyl)-5-pyridin-3-yl-1h-pyrrol-3-yl]-3-{[2(s), 3-dihydroxypropoxy]phenyl}-methanone

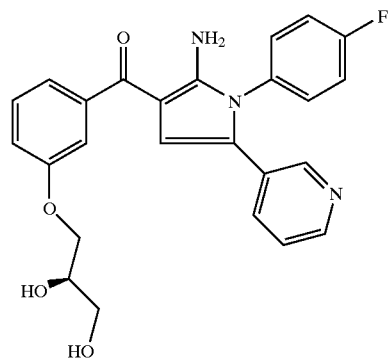

A mixture of 0.7 g (1.44 mmol) of [2-amino-1-(4-fluorophenyl)-5-pyridin-3-yl-1H-pyrrol-3-yl]-[3-(2,2-dimethyl-[1,3]dioxolan-4(S)-ylmethoxy)-phenyl]-methanone and 0.35 g of p-toluenesulfonic acid in 20 mL of methyl alcohol and 5 mL of water was heated to 50°. After 18 h, the reaction mixture was cooled to room temperature and the solvent was concentrated under reduced pressure. The residue was partitioned between aqueous sodium bicarbonate and ethyl acetate. The organic extracts were washed with brine, dried over sodium sulfate and concentrated under reduced pressure. The product was purified by flash chromatography (gradient elution: 100% ethyl acetate-10% methyl alcohol/ethyl acetate/0.4% ammonium hydroxide). The purified product was converted to a HCl salt by treatment of an ethyl acetate solution with HCl/ether. The salt was isolated by filtration and dried to give 0.4 g (56%) of 2-amino-1-(4-fluorophenyl)-5-pyridin-3-yl-1H-pyrrol-3-yl]-3-{[2(S), 3dihydroxypropoxy]phenyl}-methanone (MH$^+$=448).

Example 3

The following are representative pharmaceutical formulations containing a compound of Formula (I).

Tablet formulation
The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule formulation
The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension formulation
The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable formulation
The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
|---|---|
| Witepsol ® H-15 | balance |

Example 4

Inhibition Of p-38 (MAP) Kinase . . . In Vitro Assay

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. Biol. Chem.* Vol. 266(7), 4220–4227, (1991).

The phosphorylated form of the recombinant p38 MAP kinase was expressed with SEK-1 and MEKK in *E. Coli* and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Compounds of the invention were active in this assay. The p-38 inhibitory activities (expressed as IC$_{50}$, the concentration causing 50% inhibition of the p-38 enzyme being assayed) of some compounds of the invention are:

| Cpd # | IC$_{50}$, μM |
|---|---|
| 1 | $1.64 \times 10^{-1}$ |
| 2 | $1.69 \times 10^{-1}$ |
| 3 | $4.68 \times 10^{-1}$ |
| 4 | $1.20 \times 10^{-1}$ |

Example 5

Inhibition of LPS-Induced TNF-α Production in THP1 Cells: In Vitro Assay

The ability of the compounds of this invention to inhibit the TNF-α release may be determined using a minor modification of the methods described in described in Blifeld, C. et al. *Transplantation*, Vol. 51(2), 498–503, (1991).

(a) Induction of TNF biosynthesis

THP-1 cells were suspended in culture medium [RPMI (Gibco-BRL, Gaithersburg, Md.) containing 15% fetal bovine serum, 0.02 mM 2-mercaptoethanol], at a concentration of 2.5×10$^6$ cells/ml and then plated in 96 well plate (0.2 ml aliquots in each well). Test compounds were dissolved in DMSO and then diluted with the culture medium such that the final DMSO concentration was 5%. 20 μl aliquots of test solution or only medium with DMSO (control) were added to each well. The cells are incubated for 30 min., at 37° C. LPS (Sigma, St. Louis, Mo.) is added to the wells at a final concentration of 0.5 μg/ml, and cells are incubated for an additional 2 h. At the end of the incubation period, culture supernatants were collected and the amount of TNF-α present was determined using an ELISA assay as described below.

(b) ELISA Assay

The amount of human TNF-α present was determined by a specific trapping ELISA assay using two anti-TNF-α antibodies (2TNF-H22 and 2TNF-H34) described in Reimund, J. M., et al. GUT. Vol. 39(5), 684–689 (1996).

Polystyrene 96-well plates were coated with 50 μl per well of antibody 2TNF-H22 in PBS (10 μg/ml) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay begins at 10 ng/ml followed by 6 half log serial dilution's.

25 μl aliquots of the above culture supernatants or TNF standards or only medium (control) were mixed with 25 μl aliquots of biotinylated monoclonal antibody 2TNF-H34 (2 μg/ml in PBS containing 0.1% BSA) and then added to each well. The samples were incubated for 2 h at room temperature with gentle shaking and then washed 3 times with 0.1% BSA in PBS. 50 μl of peroxidase-streptavidin (Zymed, S. San Francisco, Calif.) solution containing 0.416 μg/ml of peroxidase-streptavidin and 0.1% BSA in PBS was added to each well. The samples were incubated for an additional 1 h at room temperature and then washed 4 times with 0.1% BSA in PBS. 50 μl of O-phenylenediamine solution (1 μg/ml O-phenylene-diamine and 0.03% hydrogen peroxide in 0.2M citrate buffer pH 4.5) was added to each well and the samples were incubated in the dark for 30 min., at room temperature. Optical density of the sample and the reference was read at 450 nm and 650 nm, respectively. TNF-α levels were determined from a graph relating the optical density at 450 nm to the concentration used.

The $IC_{50}$ value is defined as the concentration of the test compound corresponding to half-maximal reduction in 450 nm absorbance. Compounds of the invention were active in this assay.

Example 6

Inhibition of LPS-Induced TNF-α Production in Rats: In Vivo Assay

The ability of the compounds of this invention to inhibit the TNF-α release, in vivo, may be determined using a minor modification of the methods described in described in Zanetti, G.; Heumann, D., et. al., "Cytokine production after intravenous or peritoneal Gram-negative bacterial challenge in mice," J. Immunol., 148, 1890, (1992) and Sekut, L., Menius, J. A., et. al., "Evaluation of the significance of elevated levels of systemic and localized tumor necrosis factor in different animal models of inflammation," J. Lab. Clin. Med., 124, 813, (1994).

Female Sprague-Dawley rats weighing 110–140 grams (Charles River, Hollister, Calif.) are acclimated for one week. Groups containing 8 mice each are dosed orally either with the test compounds dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice are injected intraperitoneally with 50 μg/kg of LPS (Sigma, St. Louis, Mo.). After 1.5 h, the mice are sacrificed by $CO_2$ inhalation and blood is harvested by cardiocentesis. Blood is clarified by centrifugation at 15,600×g for 5 min., and sera are transferred to clean tubes and frozen at −20° C. until analyzed for TNF-α by ELISA assay (Biosource International, Camarillo, Calif.) following the manufacturer's protocol.

Example 7

Adjuvant Arthritis Assay in Rats: In Vivo Assay

The Anti-inflammatory activity of the compounds of this invention may be determined utilizing adjuvant induced arthritis in rats. Briefly, Female Sprague Dawley rats, weighing 120–155 g (Charles River, Hollister, Calif.) are acclimated in-house for approximately 1 week prior to use. On day 1, the animals are injected intradermally in the ¼ proximal portion of the tail with 0.1 ml of a mineral oil (Sigma, St. Louis, Mo.) suspension of heat killed and dried Mycobacterium Butyricum (Difco, Bacto., Des., Lot 115979JA/EXP9/99) at a concentration of 1 mg/0.1 ml.

On day 7, the test compounds are administered in CMC vehicle through to day 18. On day 18, following the administration of the compound, animals are weighed. Clinical scores are obtained to evaluate the intensity of edema in the four paws and tail. A score of 0 to 4 is assigned to each paw and 0 to 3 to the tail such that the maximum score was 19. Polyarthritic animals are scored 0 when no inflammatory signs (swelling and redness) are observed in any of the small joints (intraphalangeal, metacarpophalangeal, metatarsophalangeal) or large joints (wrist/carpus, ankle/tarsus). Animals are scored 1 when slight inflammation was observed, 2 moderate edema, 3 severe edema, and 4 when very severe edema was present. The tail is scored 0 when no signs of edema or necrotic tissue was observed, 1 when inocula injection sites and immediate surrounding tissue exhibit slight edema, 2 when approximately ¼ of the tail was either inflamed or exhibiting necrotic tissue, and 3 when over ¼ of the tail exhibited severe necroses or edema. Following clinical scores, the hind paws are transected at the distal tibia, just proximal to the tarsal joint. The left and right hind paws are weighed individually, and recorded.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of the formula:

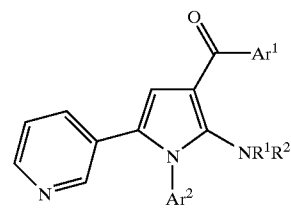

a prodrug, individual isomer, a mixture of isomers or a pharmaceutically acceptable salt thereof, wherein each of Ar¹ and Ar² is independently optionally substituted aryl; and each of R¹ and R² is independently hydrogen, alkyl or a nitrogen protecting group.

2. The compound of claim 1, wherein R¹ and R² are hydrogen.

3. The compound of claim 2, wherein Ar² is a halide substituted phenyl.

4. The compound of claim 3, wherein Ar² is 4-fluorophenyl.

5. The compound of claim 4, wherein Ar¹ is selected from the group consisting of phenyl, alkoxy substituted phenyl, hydroxy substituted phenyl and heteroalkoxy substituted phenyl.

6. The compound of claim 5, wherein Ar¹ is heteroalkoxy substituted phenyl.

7. The compound of claim 5, wherein Ar¹ is selected from the group consisting of phenyl, 3-methoxyphenyl, 3-hydroxyphenyl, and 3-(2,3-dihydroxypropoxy)phenyl.

8. A compound of claim 2, wherein Ar¹ is phenyl, alkoxy substituted phenyl, hydroxy substituted phenyl or heteroalkoxy substituted phenyl.

9. A compound of claim 8, wherein Ar¹ is heteroalkoxy substituted phenyl.

10. A compound of claim 9, wherein Ar² is 4-halophenyl.

11. A method for producing an aminopyrrole compound of the formula:

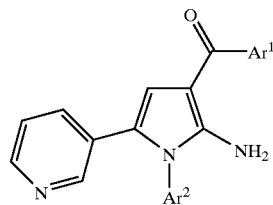

I said method comprising forming an aminopyrrole ring system by contacting a cyano compound of the formula:

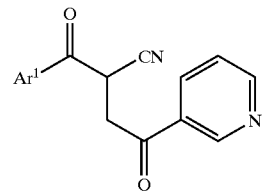

II with an arylamine compound of the formula Ar²—NH₂ under conditions sufficient to produce the aminopyrrole compound of Formula I, wherein each of Ar¹ and Ar² is independently optionally substituted aryl.

12. The method of claim 11 wherein Ar² is 4-fluorophenyl.

13. The method of claim 11 wherein Ar¹ is alkoxy substituted phenyl or heteroalkoxyphenyl.

14. A composition comprising a therapeutically effective amount of a compound of claim 1 and an excipient.

15. A method for inhibiting p38 MAP kinase in a cell comprising administering a compound of claim 1 to the cell comprising p38 MAP kinase.

16. A method for treating a disease in a mammal treatable by administration of a p38 MAP kinase inhibitor, comprising administration to the mammal a therapeutically effective amount of a compound of claim 1.

17. The method of claim 16, wherein the disease is an inflammatory disease.

18. The method of claim 17, wherein the disease is arthritis.

* * * * *